United States Patent
Chang et al.

(10) Patent No.: US 7,622,456 B2
(45) Date of Patent: Nov. 24, 2009

(54) METHOD ON CLINICAL APPLICATIONS IN HEAD NECK CANCER BY USING DSG3 MOLECULE FOR PREDICTING MALIGNANT DEGREE OF CANCER, SERVING AS A MOLECULAR TARGET AND USING RNA JAMMING SEQUENCE ON INHIBITION-SPECIFIC OF DSG3 EXPRESSION

(75) Inventors: Joseph Tung-Chieh Chang, Linkou Township (TW); Ann-Joy Cheng, Linkou Township (TW); Yin-Ju Chen, Sanchong (TW)

(73) Assignees: Non-Profit Organization Chang Gung Memorial Hospital, Taoyuan County (TW); Chang Gung University, Tao-Yuan (TW)

( * ) Notice: Subject to any disclaimer, the term of this patent is extended or adjusted under 35 U.S.C. 154(b) by 289 days.

(21) Appl. No.: 11/593,435

(22) Filed: Nov. 6, 2006

(65) Prior Publication Data

US 2009/0029354 A1    Jan. 29, 2009

(51) Int. Cl.
*A01N 43/04* (2006.01)
*A61K 31/70* (2006.01)
(52) U.S. Cl. ...................................................... 514/44
(58) Field of Classification Search ................... 514/44
See application file for complete search history.

(56) References Cited

U.S. PATENT DOCUMENTS

| | | | |
|---|---|---|---|
| 2003/0108890 A1* | 6/2003 | Baranova et al. | 435/6 |
| 2006/0019290 A1* | 1/2006 | Godfrey et al. | 435/6 |
| 2006/0241075 A1* | 10/2006 | McSwiggen | 514/44 |

* cited by examiner

*Primary Examiner*—Brian Whiteman
(74) *Attorney, Agent, or Firm*—C. G. Mersereau; Nikolai & Mersereau, P.A.

(57) ABSTRACT

The present invention provide a method for analyzing the DSG3 overexpression in tumor tissues with clinical features of cancer cells to validate that DSG3 overexpression is relates to size, depth and migration of tumor. Therefore, DSG3 overexpression is capable for using in clinical applications, determining malignant degree of tumor, serving as molecular target in Head Neck Cancer (HNC). Moreover, a jamming sequence, RNA, is designed to act on DSG3 mRNA and is effective inhibition-specific DSG3 expression, and then inhibits cell growth, invasion and migration in HNC.

1 Claim, 12 Drawing Sheets

FIG. 1A

DSG3 protein expression

FIG. 1B

```
                               A A
5' - UUGUUAAGUGCCAGACUUG   G
     AACAAUUCACGGUCUGAAG   C
                               U U
```

|  | No Metastasis | Liver Metastasis | Percentage |
|---|---|---|---|
| Vector control | 1/7 | 5/7 | 85.7% |
| DSG3-RNAi | 6/6 | 0/6 | 0% |

FIG. 9B

| Item | Number | Percentage |
|---|---|---|
| Sex | | |
| Male | 52 | 93% |
| Female | 4 | 7% |
| Age | | |
| < 40 years old | 10 | 18% |
| 41-50 years old | 17 | 30% |
| 51-60 years old | 22 | 39% |
| 61-70 years old | 6 | 11% |
| > 70 years old | 1 | 2% |
| Habits | | |
| Alcohol | 44 | 79% |
| Smoking | 51 | 91% |
| Betel quid | 50 | 89% |
| Total | 56 | 100% |

FIG. 10

| Parameter | N | DSG3 over-expression (%) | | P value |
|---|---|---|---|---|
| | | no | yes | |
| T stage | | | | |
| T1-T2 | 34 | 18 (53) | 16 (47) | 0.009 |
| T3-T4 | 22 | 4 (18) | 18 (82) | |
| N stage | | | | |
| N = 0 | 40 | 19 (47) | 21 (53) | 0.047 |
| N > 0 | 16 | 3 (19) | 13 (81) | |
| Overall stage | | | | |
| I-II | 24 | 14 (58) | 10 (42) | 0.011 |
| III-IV | 32 | 8 (25) | 24 (75) | |
| Differentiation | | | | |
| well | 27 | 8 (30) | 19 (70) | 0.153 |
| *m-p | 29 | 14 (48) | 15 (52) | |
| Tumor depth | | | | |
| < 10 mm | 19 | 12 (63) | 7 (37) | 0.009 |
| ≥ 10 mm | 37 | 10 (27) | 27 (73) | |
| Extracapsular spread in lymph nodes | | | | |
| No | 43 | 20 (47) | 23 (53) | 0.044 |
| Yes | 13 | 2 (15) | 11 (85) | |
| Total | 56 | 22(39) | 34(61) | |

*m-p: moderate to poor

FIG. 11

SEQUENCE LISTING

<160> NUMBER OF SEQ ID NOS: 1

<210> SEQ ID NO 1
<211> LENGTH: 3336
<212> TYPE: DNA
<213> ORGANISM: Human pemphigus vulgaris
<220> FEATURE:
<223> OTHER INFORMATION: NCBI Accession Number M76282; antigen mRNA
      complete cds
      gi\190751\gb\M76482\HUMPVA[190751]
<220> FEATURE:
<222> LOCATION: (2763)..(2784)
<223> OTHER INFORMATION: RNAi

<400> SEQUENCE: 1

```
ttttcttaga cattaactgc agacggctgg caggatagaa gcagcggctc acttggactt      60
tttcaccagg gaaatcagag acaatgatgg ggctcttccc cagaactaca ggggctctgg     120
ccatcttcgt ggtggtcata ttggttcatg agaattgcg aatagagact aaaggtcaat      180
atgatgaaga agagatgact atgcaacaag ctaaaagaag gcaaaaacgt gaatgggtga     240
aatttgccaa accctgcaga gaaggagaag ataactcaaa agaaaccca attgccaaga      300 ttacttcaga ttaccaagca acccagaaaa tcacctaccg aatctctgga gtgggaatcg     360
atcagccgcc ttttggaatc tttgttgttg acaaaaacac tggagatatt aacataacag     420
ctatagtcga ccgggaggaa actccaagct tcctgatcac atgtcgggct ctaaatgccc     480
aaggactaga tgtagagaaa ccacttatac taacggttaa attttggat attaatgata      540 atcctccagt attttcacaa caaattttca tgggtgaaat tgaagaaaat agtgcctcaa     600
actcactggt gatgatacta aatgccacag atgcagatga accaaccac ttgaattcta      660 aaattgcctt caaaattgtc tctcaggaac agcaggcac acccatgttc ctcctaagca      720
gaaacactgg ggaagtccgt actttgacca attctcttga ccgagagcaa gctagcagct     780
atcgtctggt tgtgagtggt gcagacaaag atggagaagg actatcaact caatgtgaat     840
gtaatattaa agtgaaagat gtcaacgata acttcccaat gtttagagac tctcagtatt     900
cagcacgtat tgaagaaaat atttaagtt ctgaattact tcgatttcaa gtaacagatt      960
tggatgaaga gtacacagat aattggcttg cagtatattt cttacctct gggaatgaag     1020 gaaattggtt tgaaatacaa actgatccta gaactaatga aggcatcctg aaagtggtga     1080
aggctctaga ttatgaacaa ctacaaagcg tgaaacttag tattgctgtc aaaacaaag     1140 ctgaatttca ccaatcagtt atctctcgat accgagttca gtcaacccca gtcacaattc     1200
aggtaataaa tgtaagagaa ggaattgcat tccgtcctgc ttccaagaca tttactgtgc     1260
aaaaaggcat aagtagcaaa aaattggtgg attatatcct gggaacatat caagccatcg     1320
atgaggacac taacaaagct gcctcaaatg tcaaatatgt catgggacgt aacgatggtg     1380 gataccctaat gattgattca aaaactgctg aaatcaaatt tgtcaaaaat atgaaccgag     1440
attctacttt catagttaac aaaacaatca cagctgaggt tctggccata gatgaataca    1500
cgggtaaaac ttctacaggc acggtatatg ttagagtacc cgatttcaat gacaattgtc     1560
caacagctgt cctcgaaaaa gatgcagttt gcagttcttc accttccgtg gttgtctccg     1620
ctagaacact gaataataga tacactggcc cctatacatt gcactggaa gatcaacctg      1680 taaagttgcc tgccgtatgg agtatcacaa ccctcaatgc tacctcggcc ctcctcagag     1740
cccaggaaca gatacctcct ggagtatacc acatctccc ggtacttaca gacagtcaga     1800
```

-continued

```
acaatcggtg tgagatgcca cgcagcttga cactggaagt ctgtcagtgt gacaacaggg  1860
gcatctgtgg aacttcttac ccaaccacaa gccctgggac caggtatggc aggccgcact  1920
cagggaggct ggggcctgcc gccatcggcc tgctgctcct tggtctcctg ctgctgctgt  1980
tggccccccct tctgctgttg acctgtgact gtggggcagg ttctactggg ggagtgacag  2040
gtggttttat cccagttcct gatggctcag aaggaacaat tcatcagtgg ggaattgaag  2100
gagcccatcc tgaagacaag gaaatcacaa atatttgtgt gcctcctgta acagccaatg  2160
gagccgattt catggaaagt tctgaagttt gtacaaatac gtatgccaga ggcacagcgg  2220
tggaaggcac ttcaggaatg gaaatgacca ctaagcttgg agcagccact gaatctggag  2280
gtgctgcagg ctttgcaaca gggacagtgt caggagctgc ttcaggattc ggagcagcca  2340
ctggagttgg catctgttcc tcagggcagt ctggaaccat gagaacaagg cattccactg  2400
gaggaaccaa taaggactac gctgatgggg cgataagcat gaattttctg gactcctact  2460
tttctcagaa agcatttgcc tgtgcggagg aagacgatgg ccaggaagca aatgactgct  2520
tgttgatcta tgataatgaa ggcgcagatg ccactggttc tcctgtgggc tccgtgggtt  2580
gttgcagttt tattgctgat gacctggatg acagcttctt ggactcactt ggacccaaat  2640
ttaaaaaact tgcagagata agccttggtg ttgatggtga aggcaaagaa gttcagccac  2700
cctctaaaga cagcggttat gggattgaat cctgtggcca tcccatagaa gtccagcaga  2760
caggatttgt taagtgccag actttgtcag gaagtcaagg agcttctgct ttgtccgcct  2820
ctgggtctgt ccagccagct gtttccatcc ctgaccctct gcagcatggt aactatttag  2880
taacggagac ttactcggct tctggttccc tcgtgcaacc ttccactgca ggctttgatc  2940
cacttctcac acaaaatgtg atagtgacag aaagggtgat ctgtcccatt tccagtgttc  3000
ctggcaacct agctggccca acgcagctac gagggtcaca tactatgctc tgtacagagg  3060
atccttgctc ccgtctaata tgaccagaat gagctggaat accacactga ccaaatctgg  3120
atctttggac taaagtattc aaaatagcat agcaaagctc actgtattgg gctaataatt  3180
tggcacttat tagcttctct cataaactga tcacgattat aaattaaatg tttgggttca  3240
taccccaaaa gcaatatgtt gtcactccta attctcaagt actattcaaa ttgtagtaaa  3300
tcttaaagtt tttcaaaacc ctaaaatcat attcgc                            3336
```

METHOD ON CLINICAL APPLICATIONS IN HEAD NECK CANCER BY USING DSG3 MOLECULE FOR PREDICTING MALIGNANT DEGREE OF CANCER, SERVING AS A MOLECULAR TARGET AND USING RNA JAMMING SEQUENCE ON INHIBITION-SPECIFIC OF DSG3 EXPRESSION

BACKGROUND OF THE INVENTION

1. Field of the Invention

The present invention relates to a DSG3 molecule that is identified the relation between the overexpression of DSG3 and the malignant degree of clinical head neck cancer (HNC), and more particularly to a method for providing a RNA jamming sequence on inhibition-specific of DSG3 expression to inhibit the growth, invasion and migration of cancer cells.

2. Description of Related Art

Head Neck Cancer (HNC) is threatening the human health seriously, the tendency on suffering from HNC is increasing year by year, and the research of HNC on the cause, diagnosis and prognosis is a very important topic therefore. There is no conventional technology by using the overexpression or underexpression of cell molecule to determine the malignant degree of cancer or be the molecular target on the therapy of HNC.

SUMMARY OF THE INVENTION

The present invention investigates and finds a DSG3 molecule relative to the HNC to study the DSG3 expression of normal and tumor tissues from 56 patients with HNC, and to identify the DSG3 overexpression is relative to the malignant degree of clinical HNC that is including the size and depth of cancer and Lymph metastasis. Therefore, the DSG3 expression is capable of determining the malignant degree of cancer on clinical applications and being a molecular target on the therapy of HNC.

The present invention also provides a method by using a RNA jamming sequence on inhibition-specific of DSG3 expression, and more particularly to a RNA jamming sequence on inhibition-specific of DSG3 mRNA expression to be identified on inhibition-specific of DSG3 protein expression effectively and then inhibit the growth, invasion and migration of cancer cells.

Further benefits and advantages of the present invention will become apparent after a careful reading of the detailed description with appropriate reference to the accompanying drawings.

DETAILED DESCRIPTION OF THE INVENTION

A. Relation Between DSG3 Expression and Clinical Malignant Degree in HNC

1. DSG3 Overexpression at both RNA and Protein Levels

Figure 1A:
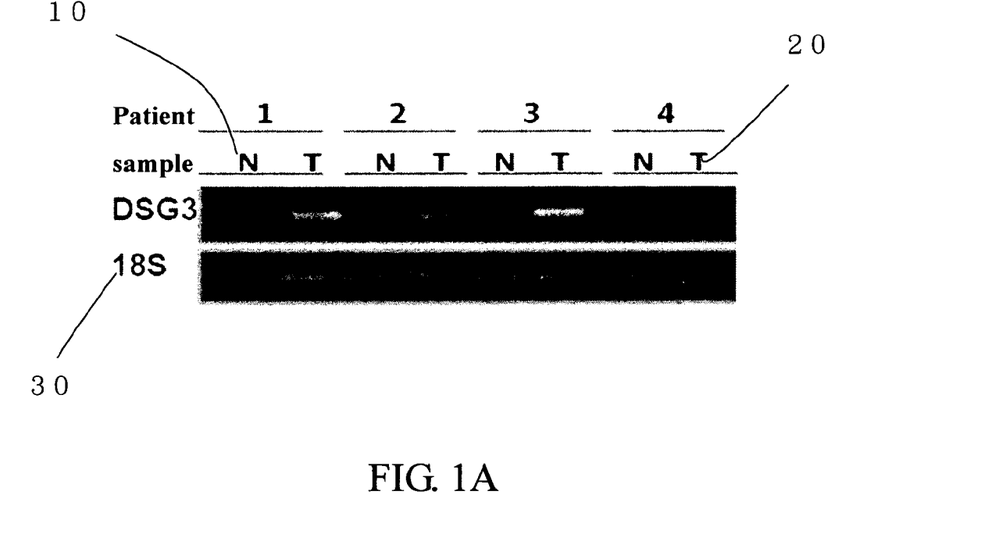
FIG. 1A shows a diagram of Gel Electrophoresis of DSG3 RNA overexpression in tumor tissue that DSG3 RNA expression as determined by PT-PCR in sample of HNC.
Figure 1B:
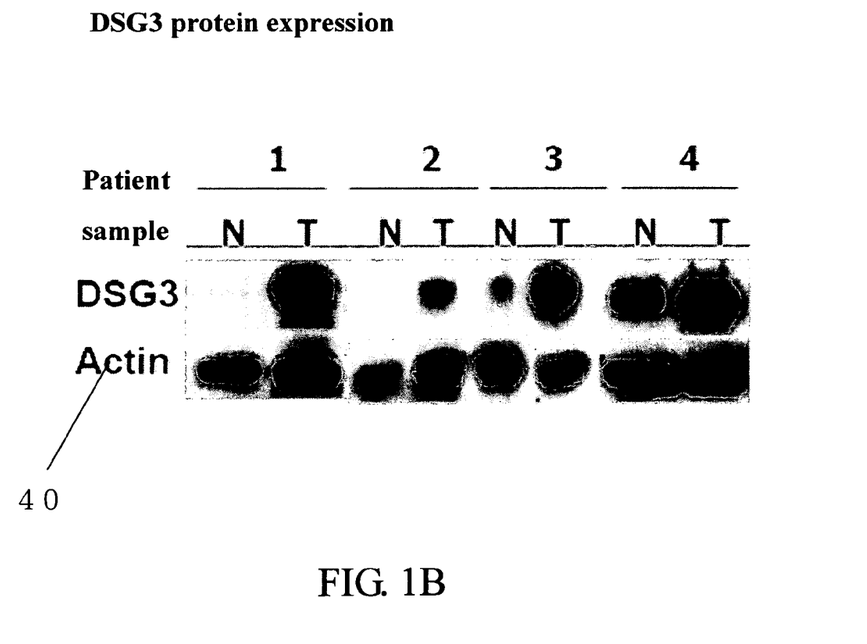
FIG. 1B shows a diagram of Gel Electrophoresis of DSG3 protein overexpression in tumor tissue that DSG3 protein expression as determined by Western blot analysis in sample of HNC.

The present invention analyses the normal and cancerous tissues to identify the DSG3 expressions at both RNA and protein levels. At RNA level, a specific sequence of DSG3 is enlarged by using Reverse Transcription-Polymerase Chain Reaction (PT-PCR) and is analyzed by Gel Electrophoresis (as shown in FIG. 1A), and the analysis at protein level uses Western blot analysis (as shown in FIG. 1B), wherein N 10 is normal tissue, T 20 is tumor tissue, 18S 30 is the expression of RNA in sample that is able to be an internal control of RNA expression, and Actin 40 is cytoskeletal protein expression that is able to be the internal control of protein expression. Regardless the RNA or protein level, DSG3 expression is higher in the tumor tissues than in the normal tissues from the same patient in the figures.

Figure 10:
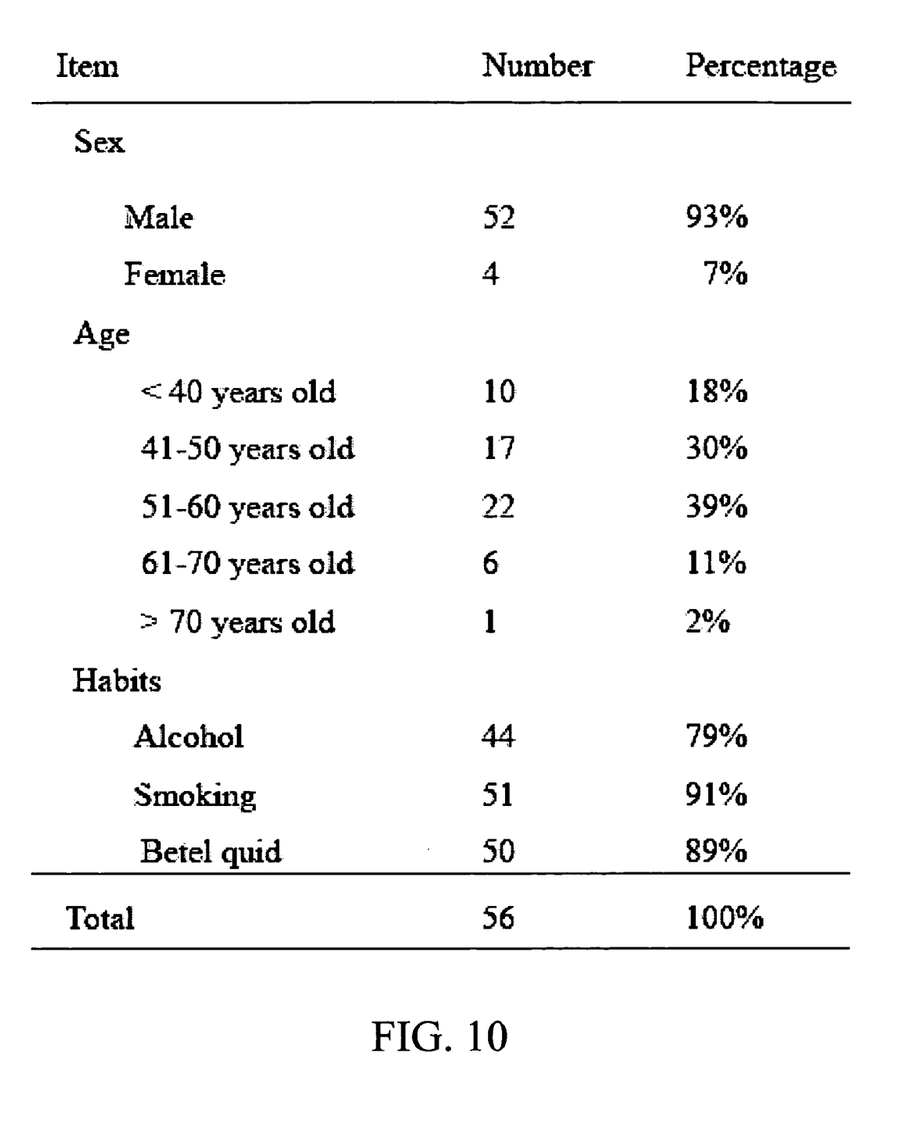
FIG. 10 shows a diagram of characteristics of HNC patients recruited in this study.

2. Method for Analyzing the Difference Between Normal and Tumor Tissues from 56 Patients with HNC Furthermore, normal and tumor tissues from 56 patients with HNC were obtained and analyzed by real time PT-PCR to identify the DSG3 expression, and the characteristics of these HNC patients were summarized in the FIG. 10. The patients included 52 (93%) males and four (7%) females, with an age range of 32-74 years (median 51 years), wherein 10 younger than 40 years old, 17 between 41 and 50 years old, 22 between 51 and 60 years old, 6 between 61 and 70 years old, and 1 older than 70 years old. A total of 44 (79%) consumed alcohol, 51 (91%) smoked tobacco and 50 (89%) chewed betel nut. The percentage of having the habits of smoking, drinking and chewing betel nut is about 80% in total patients.

The relative expression of DSG3 from each tumor sample compared with that from the normal tissue from the same patient is defined after the DSG3 RNA expression of each sample is normalized with an internal control (18S RNA expression). DSG3 expression in tumor tissue greater than twofold in the normal tissue is defined as overexpression.

Figure 11:
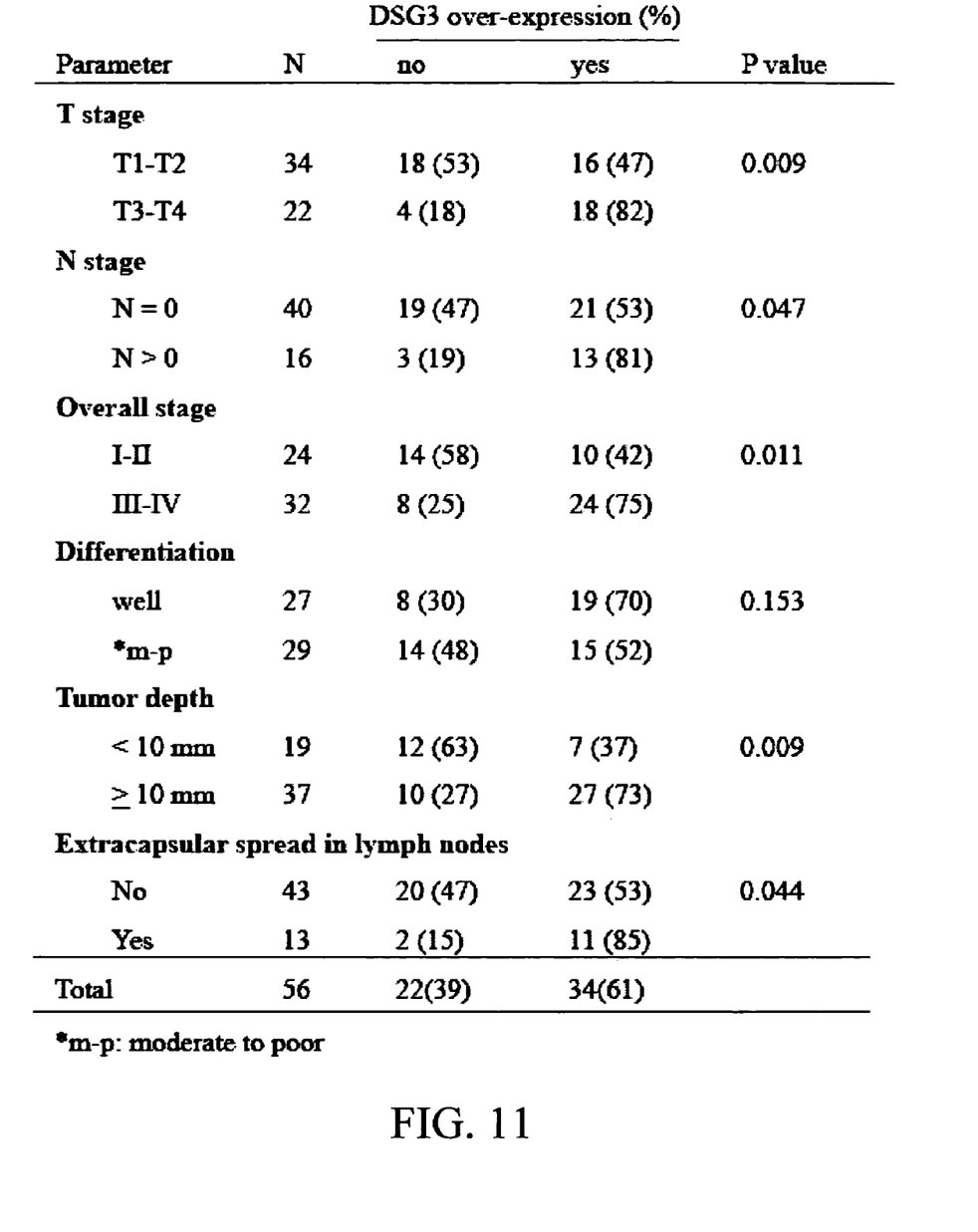
FIG. 11 shows a diagram on DSG3 expression with clinicopathologic status.

3. The Relation is Validated Between DSG3 Overexpression and Clinical Malignant Degree in HNC To compare normal tissues with tumor tissues from 56 patients with HNC, 34 patients are found that DSG3 expression in tumor tissue is higher than in normal tissue and the ratio is up to 61%. Moreover, the association of clinicopathologic features and DSG3 expression is examined by a statistical analysis and significant correlations are found between DSG3 overexpression and T stage (P=0.009), N stage (P=0.047), overall stage (P=0.011), tumor depth (P=0.009) and extracapsular spread in lymph nodes (P=0.044) (as shown in FIG. 11), wherein DSG3 overexpressions on T stage and overall stage suggest that DSG3 participate in cancer growth and DSG3 overexpressions on N stage, tumor depth and extracapsular spread in lymph nodes suggest that DSG3 participate in cancer invasion. Accordingly, the present invention validates that DSG3 expression is relative to the clinical malignant degree in HNC and DSG3 overexpression is able to be used on the clinical application for determining the malignant degree of cancer or be the molecular target on the therapy of HNC.

B. Method for Providing a RNA Jamming Sequence on Inhibition-Specific of DSG3 Expression 1. Mechanism of RNA Interference The mechanism of RNA interference is that a little clone of RNA (about 17 ~22 pieces of Nucleotide) combines with message RNA (mRNA) in cells through sequence matching, is identified by protein Dicer in cells, attracts RISC enzyme, and then the RNA is decomposed to accomplish the inhibition-specific of DSG3 expression. However, the inhibition effect of RNA interference greatly depends on the sequence of the little clone of RNAi transfected into the cells, and the present invention finds a clone of sequence-specific (DSG3-RNAi) in DSG3 molecules that is capable of inhibiting DSG3 expression effectively.

2. Design Process and Method of DSG3-RNAi

The inhibition of DSG3 reduces cell growth and colony formation by the interference of a clone of sequence, and the clone of sequence is named DSG3-RNAi. The DSG3-RNAi is situated from the 2761st Nucleotide towards 3'-downstream to the 18th Nucleotide in DSG3 mRNA and has the sequence of 5'-TTGTTAAGTGCCAGACTT-3' (SEQ. ID. NO. 2) to act on DSG3 mRNA. The experiment method is as follows:

(1) Two Clones of DSG3-RNAi Sequences is Synthesized in the Structure of Symmetrical Complementary Sequence (SEQ. ID. NO. 3)
5'-GGATTTGTTAAGTGCCAGACTTgaagcttgAAGTCTGGCACTTAACAAATCC-3'

(SEQ. ID. NO. 4)
5'-GGATTTGTTAAGTGCCAGACTTcaagcttcAAGTCTGGCACTTAACAAATCC-3'

(2) The Synthesized Sequence is Linked into an Expression Vector

The two clones of synthesized Nucleotide RNAi sequences are heated individually at 95° C. for 10 min and cooled slowly at room temperature for the matching of the two clones of synthesized sequences, and then the expression vector is cleaved by using restriction enzyme and is inserted the two clones of RNAi sequences individually to form DSG3-RNAi plasmid by using T4 DNA ligase assembly. The assembled sequence expresses in coliform and the DSG3-RNAi plasmid is extracted for different applications.

3. DSG3-RNAi is Validated on Inhibition-Specific of DSG3 Expression

Figure 2:
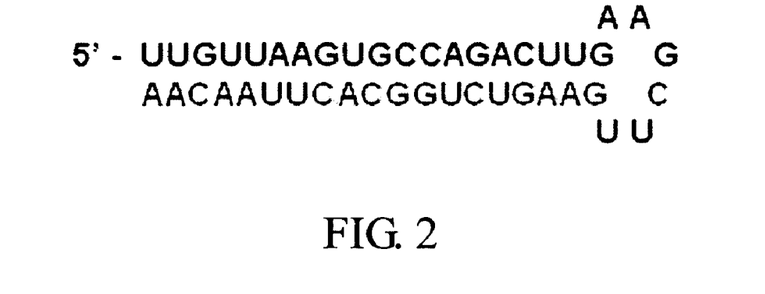
FIG. 2 shows a diagram of hairpin structure by DSG3 RNA interference in HNC (SEQ. ID. NO. 6).

The DSG3-RNAi plasmid and a vector (hereinafter, inscribed as "vector control") that has no suppression sequence are transfected into cell lines, and DSG3-RNAi plasmid forms a special hairpin structure in cell lines after transcription (as shown in FIG. 2).

Figure 3A:
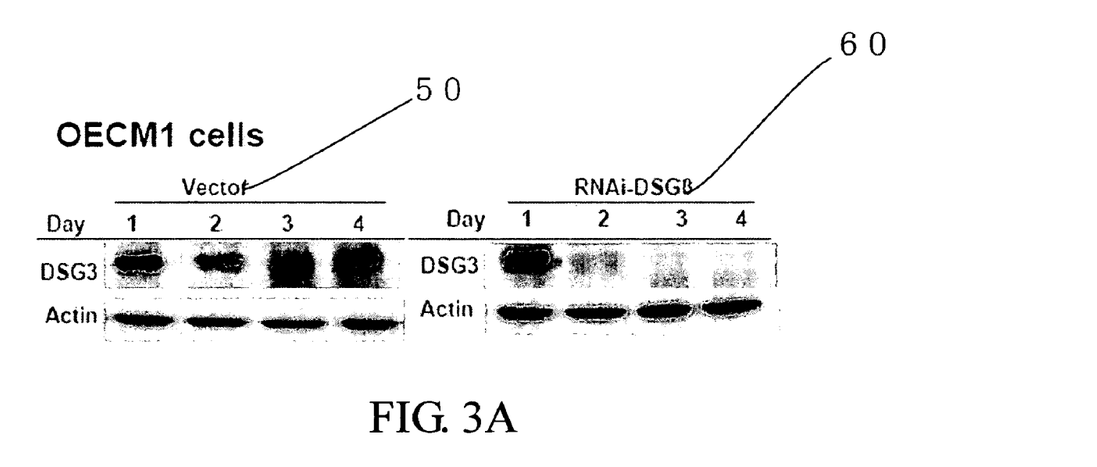
FIG. 3A shows a diagram on effects of DSG3-RNAi on DSG3 protein expression in OECM1 cells, and cells are transfected with DSG-RNAi and further cultured for 4 days.
Figure 3B:
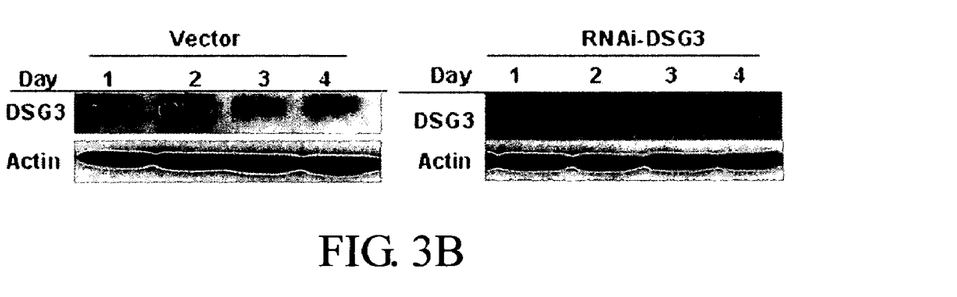
FIG. 3B shows a diagram on effects of DSG3-RNAi on DSG3 protein expression in BM1 cells, and cells are transfected with DSG-RNAi and further cultured for 4 days.

Effects of DSG3-RNAi on DSG3 expression in HNC cell lines such as OEC-M1 and BM1 are analyzed by Western blot analysis to compare with DSG3 expression in a vector control 50 through extracting proteins in cell lines. Referring to FIGS. 3A and 3B that show the results after 2 days, the results indicate DSG3 expression is inhibited in DSG3-RNAi for 4 days. An actin protein expression serves as an internal control and there is no effect of DSG3-RNAi on actin expression as shown in FIGS. 3A and 3B. The results validate that DSG3-RNAi sequence is able to be inhibition-specific on DSG3 expression.

C. DSG3-RNAi is Specifically Inhibiting the Malignant Proliferation and Invasion Migration of Cancer Cells.

1. DSG3 Knockdown Inhibits Cell Growth in HNC Cell Lines.

Figure 4A:
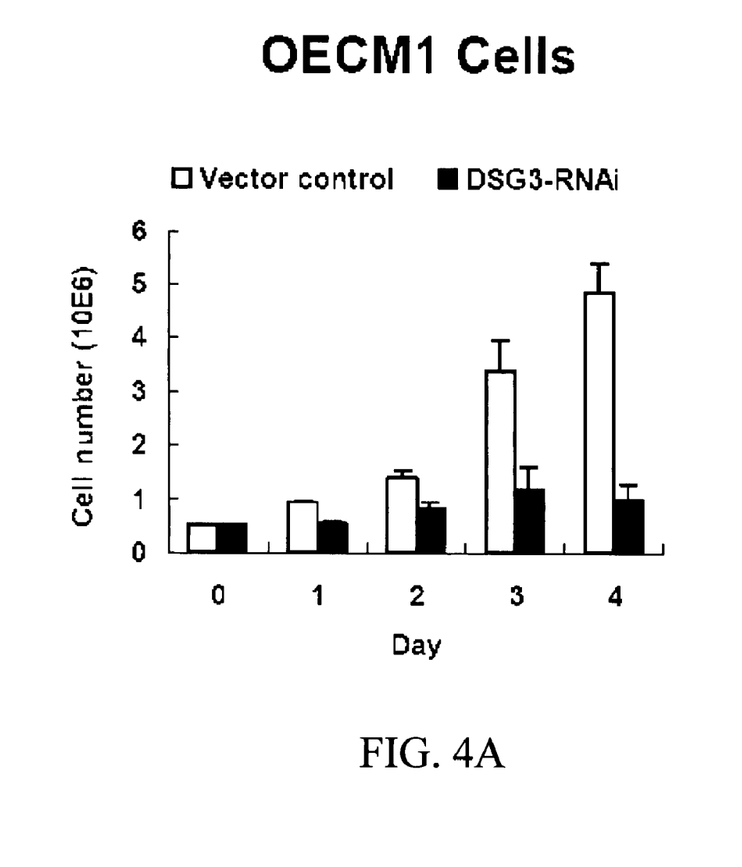
FIG. 4A shows a diagram that DSG3 knockdown inhibits cell growth in OECM1 cell lines, and cells are transfected with DSG-RNAi and further cultured for 4 days.
Figure 4B:
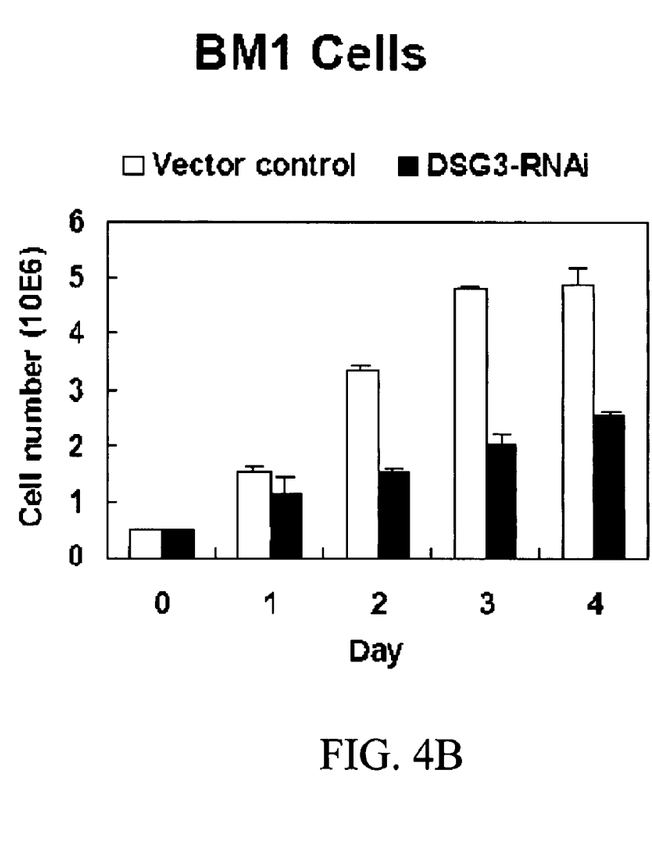
FIG. 4B shows a diagram that DSG3 knockdown inhibits cell growth in BM1 cell lines, and cells are transfected with DSG-RNAi and further cultured for 4 days.

DSG3-RNAi sequence-specific is transfected into cancer cell lines and effects of DSG3-RNAi on cell growth in HNC cell lines are observed to compare with the vector control. The variation of cell growth is observed by counting cell numbers for 4 days, results are shown in FIGS. 4A and 4B. Referring to FIGS. 4A and 4B, the results indicate that knockdown of DSG3 expression inhibits cell growth in HNC cell lines.

2. DSG3 Knockdown Inhibits Colony Formation in HNC Cell Lines.

Figure 5A:
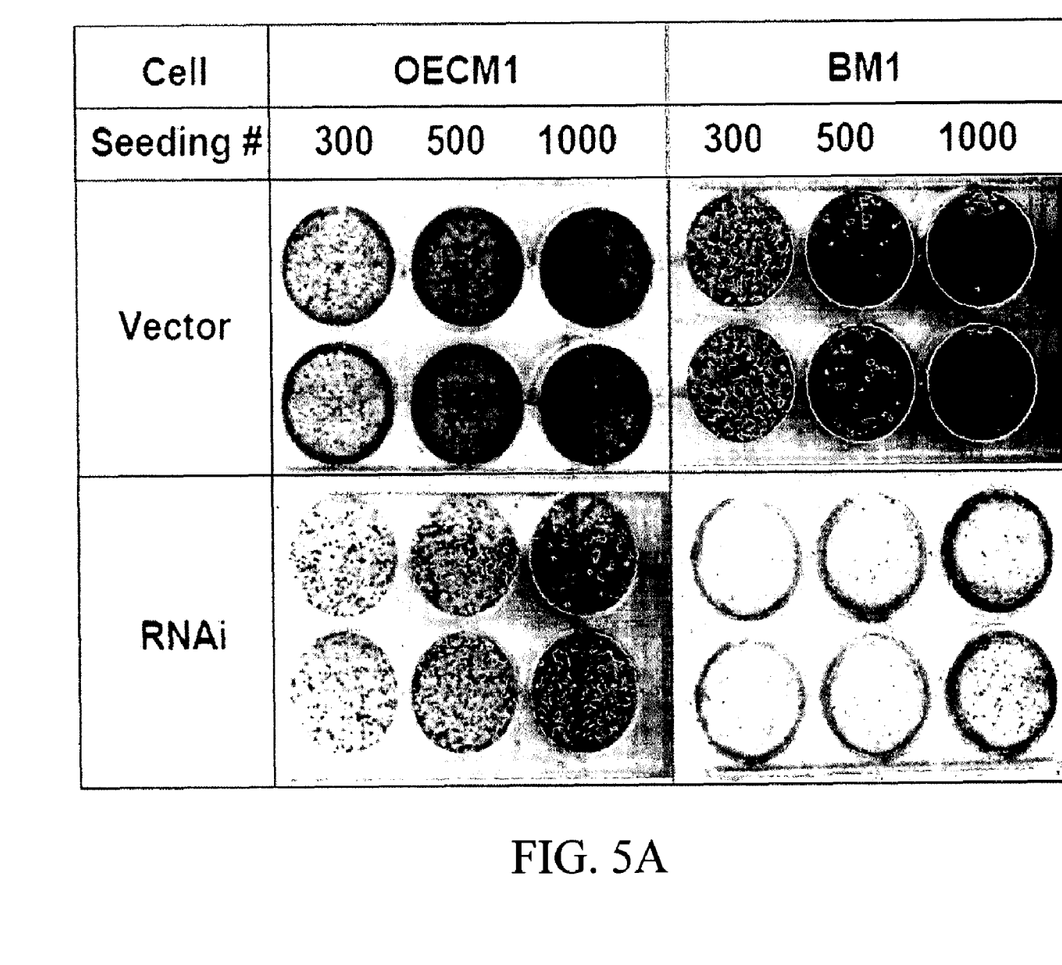
FIG. 5A shows a diagram of cell analysis to indicate that DSG3 knockdown inhibits colony formation in OECM1 and BM1 cell lines.
Figure 5B:
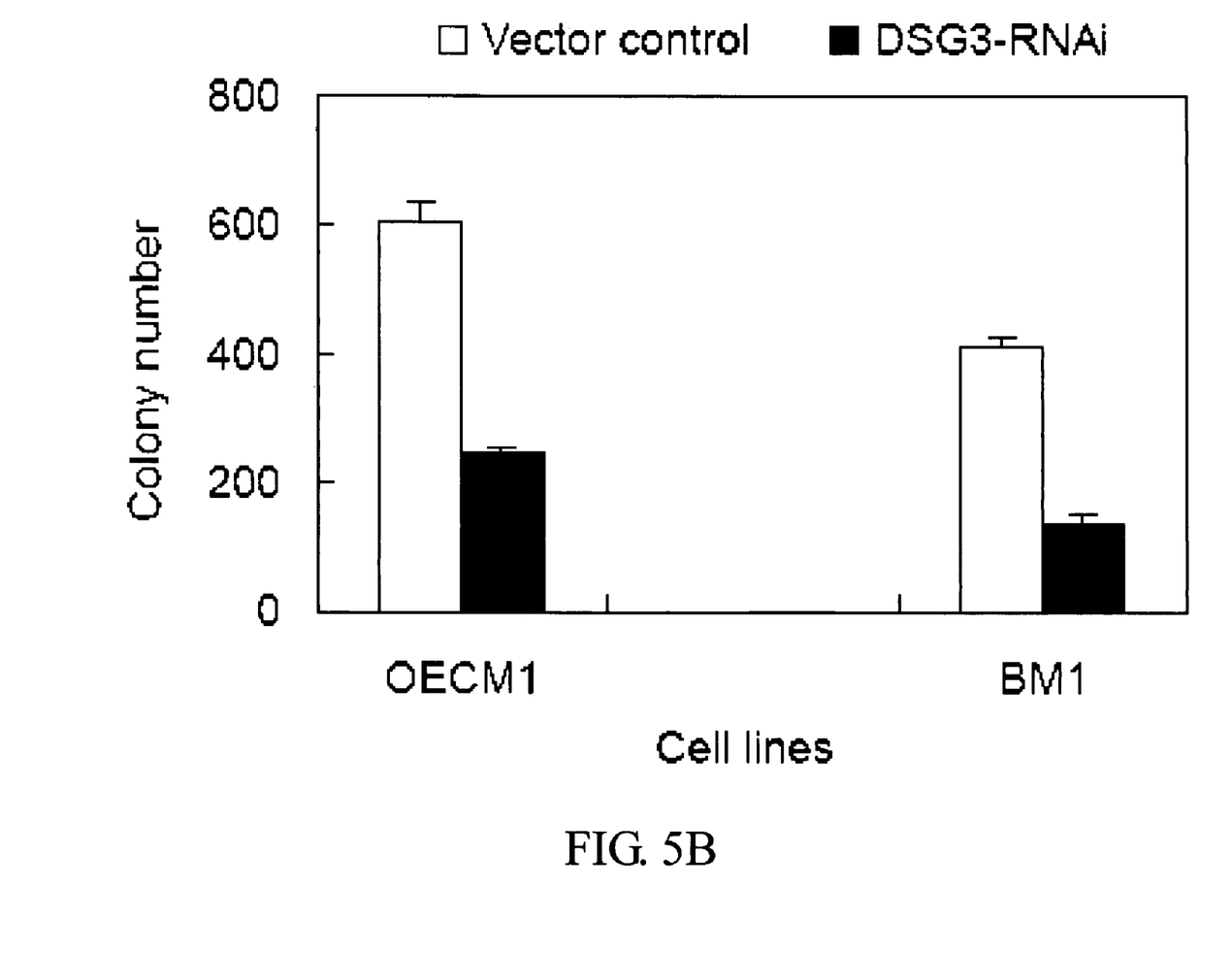
FIG. 5B shows a diagram on quantitative determination of colony numbers to indicate that DSG3 knockdown inhibits colony formation in OECM1 and BM1 cell lines.

Cellular colony formation is determined by colony formation assay, and the assay is investigated and observed by photograph observation and quantitative colony numbers as shown in FIG. 5A, and FIG. 5B is quantitative determination of colony numbers on colony formation. In the experiments on oral carcinoma cells (OECM1) and nasopharynmeal carcinoma cells (BM1) respectively, the colony numbers and size of carcinoma cells are less and smaller than vector control after transfection with DSG3-RNAi and various numbers of cells (300-1000 for OECM1 and BM1) are seeded. Referring to FIG. 5A, the colony numbers and size of carcinoma cells are less and smaller than vector control after DSG3 expression is inhibited by DSG3-RNAi, and 500 cells are seeded for quantitative assay and results are shown in FIG. 5B that is quantitative assay of cellular colony formation. In the experiments on OECM1 and BM1 respectively, the colony numbers and size of carcinoma cells are less and smaller than vector control after transfection with DSG3-RNAi and 500 cells for OECM1 and BM1 are seeded. The foregoing both two kinds of experiments validate that knockdown of DSG3 expression inhibits cell growth in HNC cell lines.

3. DSG3 Knockdown Inhibits Cell Migration in HNC Cell Lines

Figure 6:
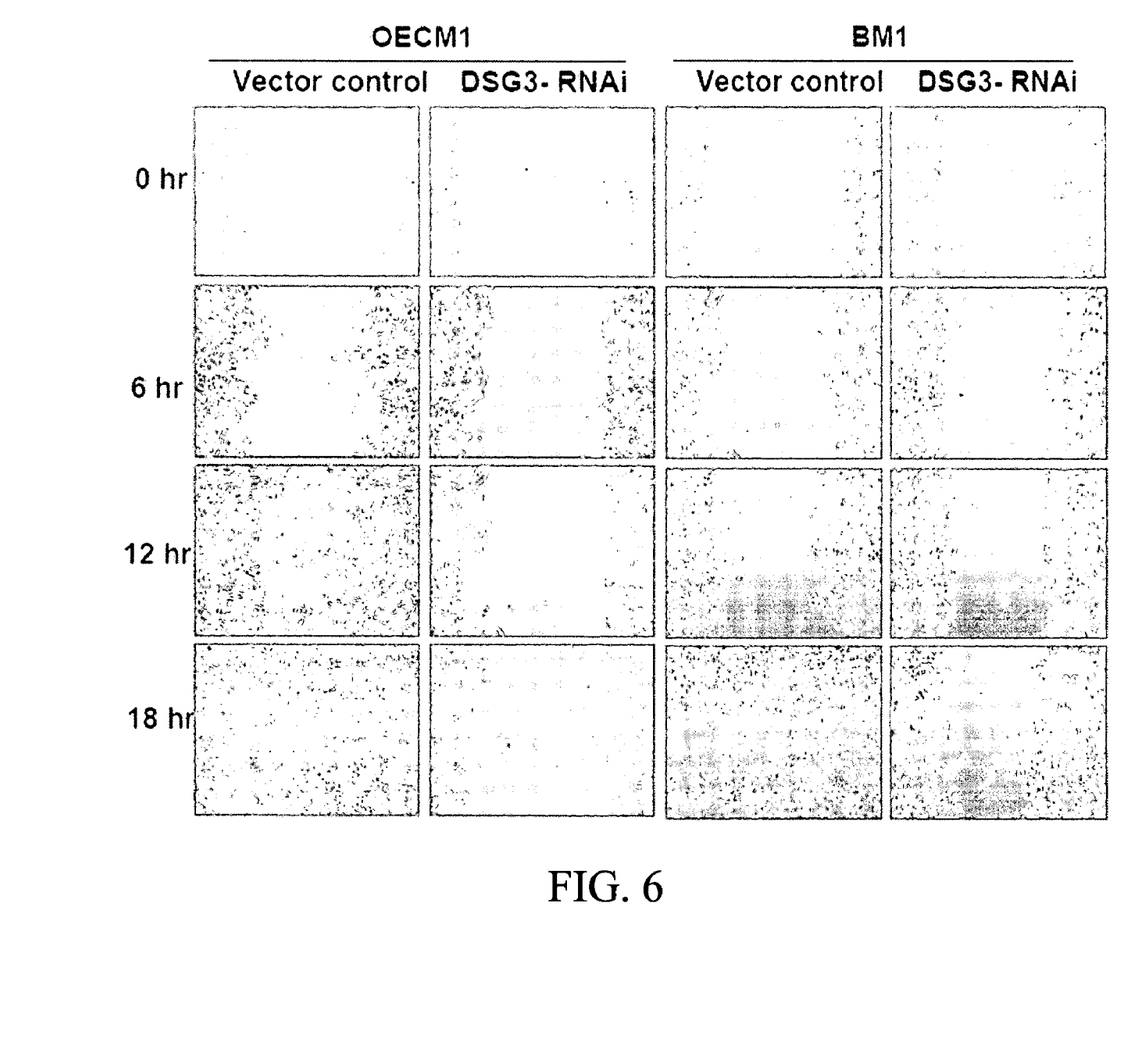
FIG. 6 shows a diagram in vitro wounded healing assay to indicate that DSG3 knockdown reduces cell migration in OECM1 and BM1 cell lines.

After DSG3-RNAi is transfected into HNC cell lines, cell migration is determined using in vitro wound healing assays to observe and compare effects of cell migration and invasion with vector control as shown in FIG. 6. In the experiments on OECM1 and BM1 in vitro wound healing assays respectively, cells are wounded by a micropipette tip and cell migration toward the wounded is observed. Referring to FIG. 6, DSG3-RNAi is able to inhibit cell migration compared with vector control in OECM1 and BM1 cell lines 4. DSG3 Knockdown Inhibits Cell Invasion in HNC Cell Lines.

Figure 7A:
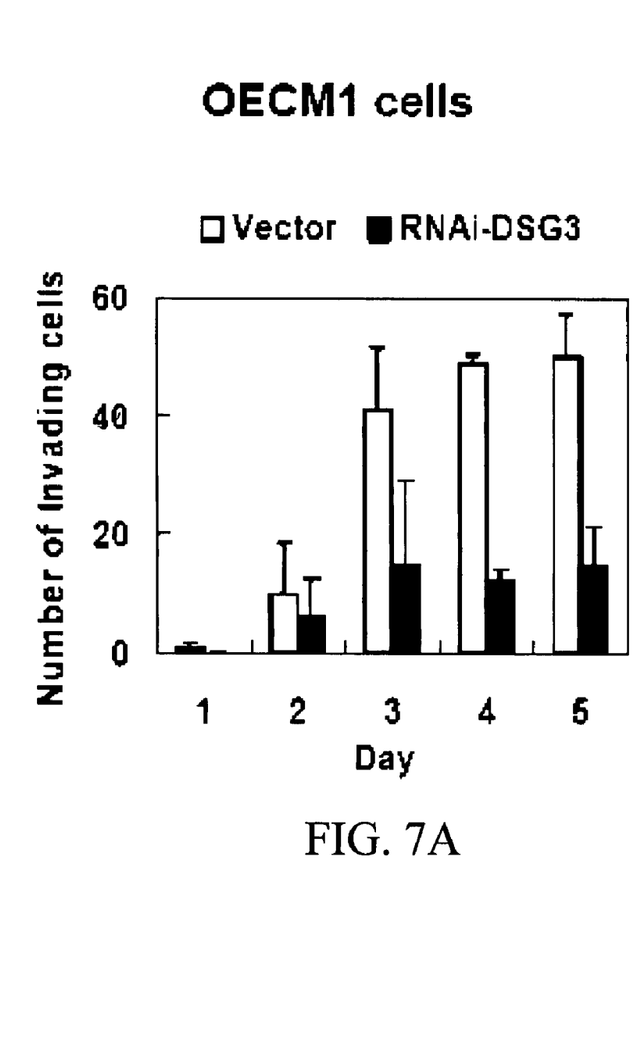
FIG. 7A shows a diagram in vitro Matrigel Transwell invasion assays to indicate that DSG3 knockdown reduces cell migration in OECM1 cell lines.
Figure 7B:
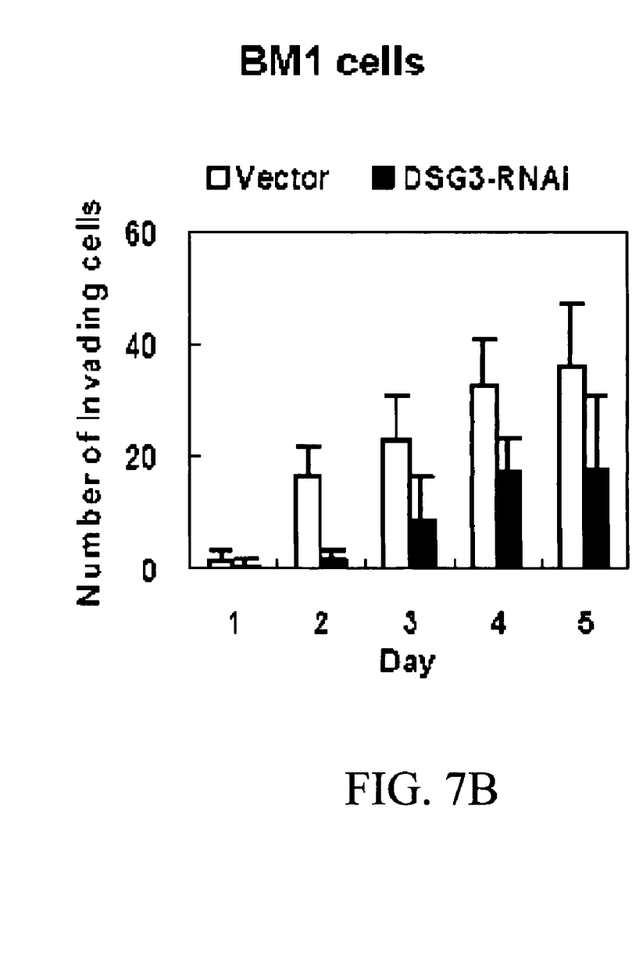
FIG. 7B shows a diagram in vitro Matrigel Transwell invasion assays to indicate that DSG3 knockdown reduces cell migration in BM1 cell lines.

Similarly, cell invasion is determined using in vitro Matrigel Transwell invasion assays to analyze and quantify the penetration ability of cells by counting the cell numbers that penetrate Matrigel for 5 days and the results show in FIGS. 7A and 7B. In the experiments on OECM1 and BM1 in vitro Matrigel Transwell invasion assays respectively, cell invasion is determined by observing cell numbers that penetrate Matrigel for 5 days and the results indicate that DSG3-RNAi apparently inhibits the ability of cell invasion compared with vector control in OECM1 and BM1 cell lines as shown in FIGS. 7A and 7B. In FIGS. 7A and 7B, the numbers of carcinoma cells that penetrate Matrigel are less than vector control after DSG3 expression is inhibited by DSG3-RNAi and the foregoing both two kinds of experiments validate that knockdown of DSG3 expression inhibits the abilities of cell migration and invasion in HNC cell lines.

5. DSG3 Knockdown Inhibits Cancer Cell Growth In Vivo.

Figure 8A:
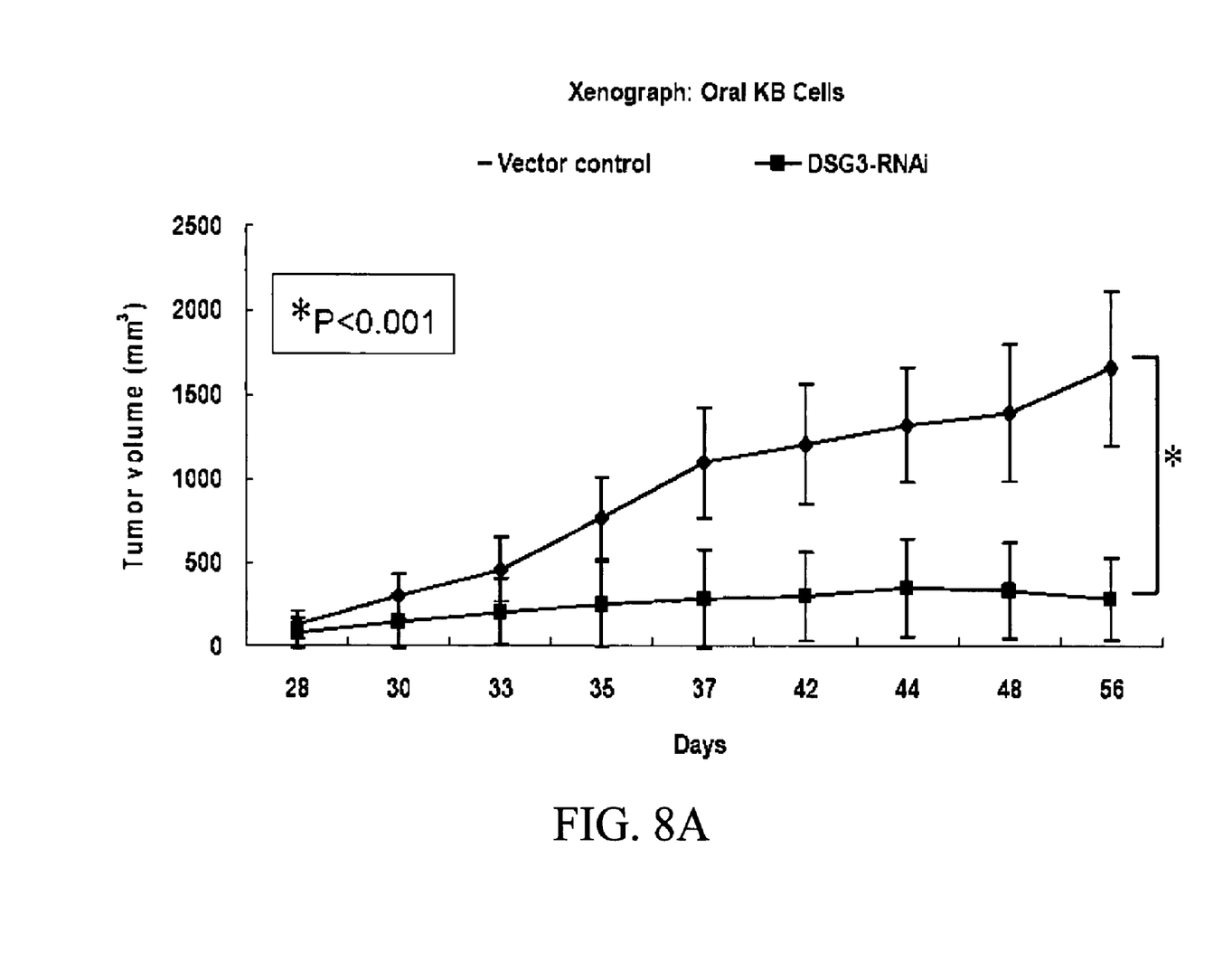
FIG. 8A shows a diagram of effect of DSG3-RNAi on tumor xenograft BALB-C/nu mice to validate that DSG3 Knockdown inhibits cancer cell growth in vivo.
Figure 8B:
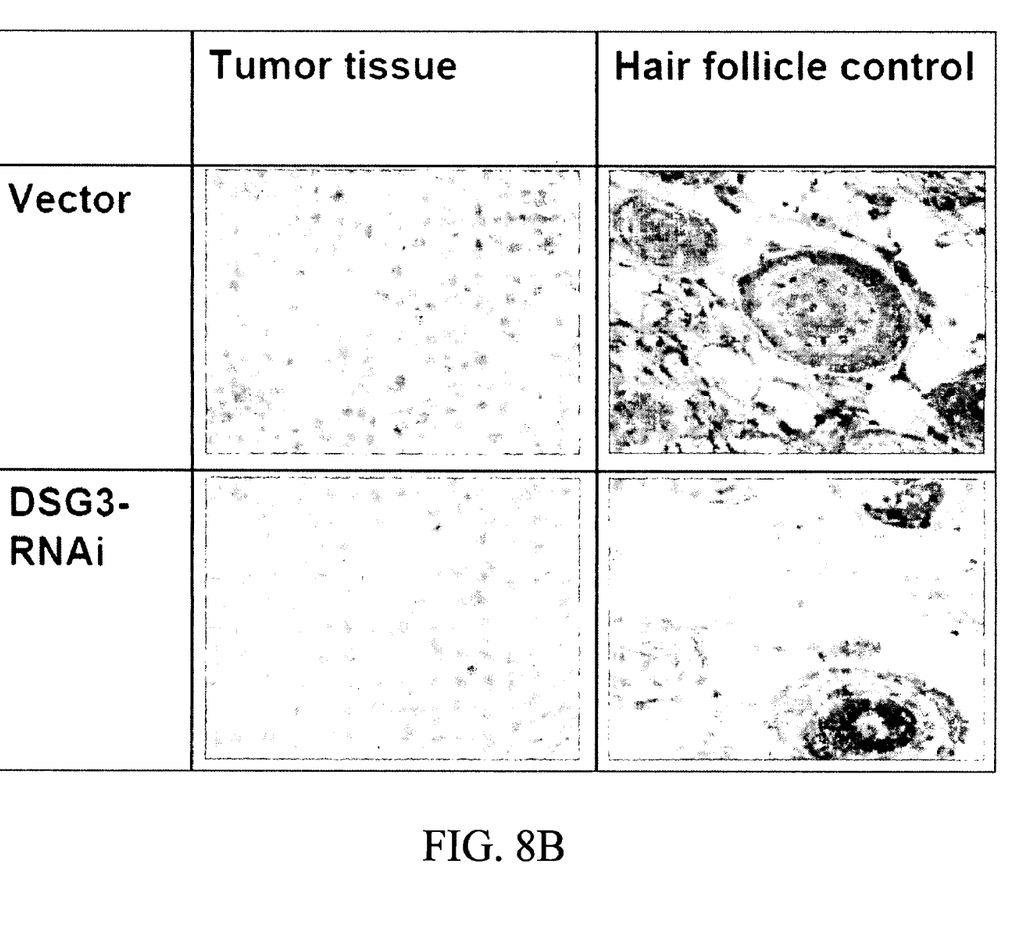
FIG. 8B shows a diagram of immunohistochemical (IHC) analysis to validate that DSG3 expression is certainly inhibited by DSG3-RNAi

The experiment is to validate that DSG3 knockdown inhibits cancer cell growth in vivo animal and the BALB/C-nu nude mice at 5 weeks of age are used for the experiment. The mice are subcutaneously injected with $10^7$ cancer cell lines and are intravenously injected 50 µg of control vector or DSG3-RNAi plasmid after 3 days, followed by a booster of 25 µg of vector or plasmid twice a week for a total 6 weeks. Each treatment group has five mice, the cancer cells are monitored for a total of 60 days and then the cancer cell volume is calculated as length×width×height and results are shown in FIG. 8A. In vector control, the cancer cell growth is continuous, but DSG-RNAi apparently inhibits the cancer cell growth. Besides, six weeks after grafting, cancer cells are removed and observed on DSG3 expression and hair follicle tissues were also stained as internal control. The results validate that DSG3 expression is certainly inhibited by DSG3-RNAi (as shown in FIG. 8B), and that DSG3 knockdown inhibits cancer cell growth is validated.

6. DSG3 Knockdown Inhibits Cancer Cell Migration In Vivo.

Figure 9A:
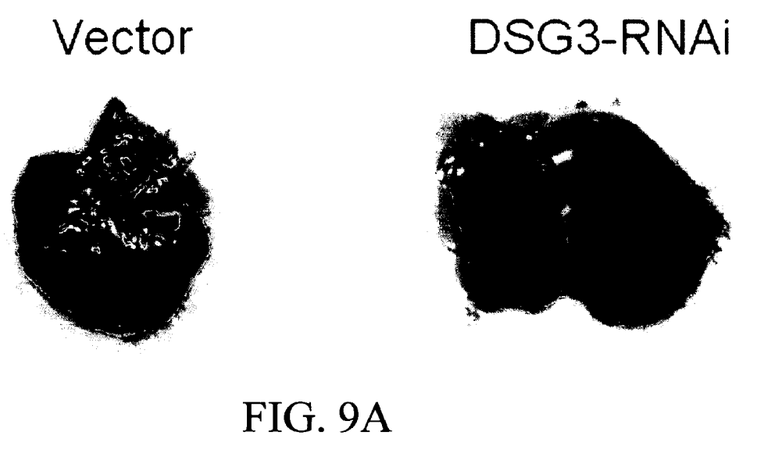
FIG. 9A shows a diagram of liver organ to validate that DSG3 Knockdown inhibits cancer migration in vivo.
Figure 9B:
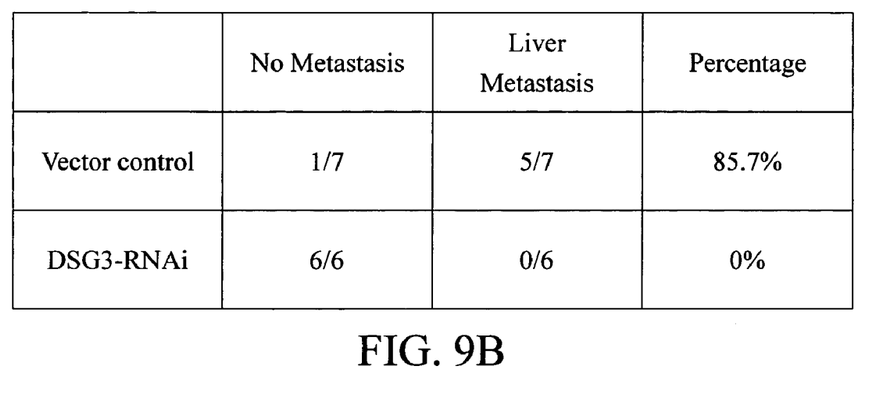
FIG. 9B shows a diagram of statistical table to indicate that DSG3 Knockdown inhibits cancer migration in vivo

The experiment is to validate that DSG3 knockdown inhibits cancer cell migration in vivo animal and the BALB/C-nu nude mice at 5 weeks of age are used for the experiment. The mice are intravenously injected with 5×106 cancer cell lines so as to simulate that cancer cells flow into blood and observe if cancer cells migrate to liver and are intravenously injected 50 µg of control vector or DSG3-RNAi plasmid after 3 days, followed by a booster of 25 µg of vector or plasmid twice a week for a total 3 weeks. The vector control group has seven mice and the experimental group has six mice, the cancer cells are monitored for a total of 30 days and then the livers are took out by sacrificing the mice to be observed and determined the hepatic migration. Referring to FIG. 9A, there are a plurality of yellowish-white cancer cells at the liver in vector control group, and there is no hepatic migration in the experimental group that using reagents. The statistical table is shown in FIG. 9B that six mice display hepatic migration (85.7%) in vector control group and no mouse displays hepatic migration (0%) in experimental group. The results validate that DSG3 Knockdown inhibits cancer cell migration.

Known by the aforesaid, the present invention provides a method for clinical or prognosis applications on determining the malignant degree of HNC including tumor size, Lymph invasion, tumor depth and cancer stage by determining DSG3 expression. The present invention also provides a RNA jamming sequence, DSG3-RNAi sequence, on inhibition-specific of DSG3 expression for inhibiting DSG3 expression and then inhibiting cell growth and invasion in HNC. Therefore, the DSG3-RNAi sequence is applied on the development of cancer medicine, the RNAi that act on DSG3 mRNA is 5'-TTGTTAAGTGCCAGACTT-3'.

A method for providing a RNA jamming sequence on inhibition-specific of DSG3 expression to inhibit the growth of cancer cells, comprising the steps of:

(a) designing the jamming sequence, named DSG3-RNAi, so as to interfere DSG3 expression, wherein the DSG3-RNAi is situated from the 2761st Nucleotide towards 3'-downstream to the 18th Nucleotide in DSG3 mRNA and is 5'-TTGTTAAGTGCCAGACTT-3'; (SEQ. ID. NO. 2)

(b) synthesizing two clones of DSG3-RNAi sequences in the structure of symmetrical complementary sequence, such as (SEQ. ID. NO. 3)
5'-GGATTTGTTAAGTGCCAGACTTgaagcttgAAGTCTGGCACTTAACA
AATCC-3'

(SEQ. ID. NO. 4)
5'-GGATTTGTTAAGTGCCAGACTTcaagcttcAAGTCTGGCACTTAACA
AATCC-3';

(c) linking the synthesized sequence into an expression vector by the ways of matching the two clones of Nucleotide RNAi sequences, cleaving the expression vector via using restriction enzyme, inserting the two clones of RNAi sequences into the expression vector respectively to assemble and form DSG3-RNAi plasmid, and extracting the DSG3-RNAi plasmid via expressing the assembled sequence in coliform;

(d) transfecting the DSG3-RNAi plasmid into cell lines so as to form a special hairpin structure in cell lines after transcription; and (e) transfecting the DSG3-RNAi plasmid into cancer individuals respectively for inhibiting cell growth of cancer.

A suppression reagent that is a DSG3-RNAi plasmid for injecting into cancer individuals, wherein the DSG3-RNAi plasmid is a DSG3-RNAi sequence and the DSG3-RNAi sequence is 5'-TTGTTAAGTGCCAGACTT-3' (SEQ. ID. NO. 2) to synthesize two clones of DSG3-RNAi sequences in the structure of symmetrical and then link the synthesized sequence into an expression vector.

Although the present invention has been explained in relation to its preferred embodiments, it is to be understood that many other possible modifications and variations can be made without departing from the spirit and scope of the invention as hereinafter claimed.

What is claimed is:

1. A method for inhibiting DSG3 expression in cancer individuals by using a RNA jamming sequence to inhibit cell growth, invasion and migration in head neck cancer (HNC), wherein the method comprises the steps of:
   (a) designing a RNA jamming sequence, named DSG3-RNAi, wherein the DSG3-RNAi is set forth in SEQ ID NO: 2;
   (b) synthesizing two clones of DSG3-RNAi comprising SEQ ID NO: 2 in the structure of symmetrical complementary sequence, wherein one clone is set forth in SEQ ID NO: 3 and the other clone is set forth in SEQ ID NO: 4;
   (c) linking SEQ ID NO: 3 and SEQ ID NO: 4 into an expression vector and making a plasmid comprising the expression vector;
   (d) transfecting the plasmid into cancer individuals respectively for inhibiting cell growth of cancer.

* * * * *